US012788383B2

(12) United States Patent
Erzberger

(10) Patent No.: US 12,788,383 B2
(45) Date of Patent: Nov. 10, 2026

(54) MEDICAL DEVICE HAVING EXPANDABLE AND COLLAPSIBLE OCCLUDING MEMBERS FOR TREATMENT OF ATRIAL SEPTAL DEFECTS

(71) Applicant: St. Jude Medical, Cardiology Division, Inc., St. Paul, MN (US)

(72) Inventor: Gary Erzberger, Corcoran, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 611 days.

(21) Appl. No.: 18/060,315

(22) Filed: Nov. 30, 2022

(65) Prior Publication Data

US 2023/0165576 A1 Jun. 1, 2023

Related U.S. Application Data

(60) Provisional application No. 63/284,075, filed on Nov. 30, 2021.

(51) Int. Cl.
*A61B 17/00* (2006.01)

(52) U.S. Cl.
CPC *A61B 17/0057* (2013.01); *A61B 2017/00592* (2013.01); *A61B 2017/00597* (2013.01); *A61B 2017/00601* (2013.01); *A61B 2017/00606* (2013.01); *A61B 2017/00619* (2013.01); *A61B 2017/00623* (2013.01)

(58) Field of Classification Search
CPC ...... A61B 17/0057; A61B 2017/00592; A61B 2017/00601; A61B 2017/00623; A61B 2017/00597; A61B 2017/00606; A61B 2017/00619
See application file for complete search history.

(56) References Cited

U.S. PATENT DOCUMENTS

| | | | |
|---|---|---|---|
| 3,874,388 | A | 4/1975 | King et al. |
| 5,171,259 | A | 12/1992 | Inoue |
| 6,077,281 | A | 6/2000 | Das |
| 8,764,848 | B2 | 7/2014 | Callaghan |
| 8,992,545 | B2 | 3/2015 | Cahill |

(Continued)

FOREIGN PATENT DOCUMENTS

| | | | |
|---|---|---|---|
| CN | 108888302 | A | 11/2018 |
| DE | 102010019365 | A1 | 6/2011 |

(Continued)

*Primary Examiner* — Jing Rui Ou
(74) *Attorney, Agent, or Firm* — SLEMAN & LUND LLP

(57) ABSTRACT

A medical device for treating an atrial septal defect (ASD) includes a first occluding member, and a second occluding member disposed in opposition to the first occluding member. The medical device also includes at least one elongate shaft extending through and between the first occluding member and the second occluding member. The first occluding member is foldable to expand and contract relative to the second occluding member. The second occluding member is foldable to expand and contract relative to the first occluding member. In operation, at least one of the first occluding member and the second occluding member is configured to expand relative to the other of the first occluding member and the second occluding member to treat the ASD at the target site.

13 Claims, 7 Drawing Sheets

(56) References Cited

U.S. PATENT DOCUMENTS

| | | | | |
|---|---|---|---|---|
| 2003/0139819 | A1* | 7/2003 | Beer | A61B 17/0057 623/23.71 |
| 2004/0143277 | A1 | 7/2004 | Marino et al. | |
| 2004/0220610 | A1* | 11/2004 | Kreidler | B32B 27/08 606/151 |
| 2005/0065548 | A1* | 3/2005 | Marino | A61B 17/0057 606/213 |
| 2006/0265004 | A1* | 11/2006 | Callaghan | A61B 17/50 606/213 |
| 2007/0244517 | A1* | 10/2007 | Callaghan | A61B 17/0057 606/213 |
| 2009/0012559 | A1 | 1/2009 | Chanduszko | |
| 2014/0155932 | A1* | 6/2014 | Weishaupt | A61B 17/0057 606/200 |
| 2017/0105711 | A1* | 4/2017 | Masters | A61B 90/39 |
| 2018/0333150 | A1 | 11/2018 | Bak-Boychuk | |
| 2019/0328374 | A1 | 10/2019 | Hendsbee | |
| 2021/0059684 | A1 | 3/2021 | Meyer | |

FOREIGN PATENT DOCUMENTS

| | | | |
|---|---|---|---|
| JP | 2009000497 | A | 1/2009 |
| TR | 201818040 | T4 | 12/2018 |
| WO | 2005074813 | A1 | 8/2005 |
| WO | 2012156415 | A1 | 11/2012 |

* cited by examiner

MEDICAL DEVICE HAVING EXPANDABLE AND COLLAPSIBLE OCCLUDING MEMBERS FOR TREATMENT OF ATRIAL SEPTAL DEFECTS

CROSS-REFERENCE TO RELATED APPLICATIONS

This application claims the benefit of priority to U.S. Provisional Patent Application No. 63/284,075, filed on Nov. 30, 2021, which is incorporated herein by reference in its entirety.

BACKGROUND OF THE DISCLOSURE

A. Field of Disclosure

The present disclosure relates generally to medical devices that are used in the human body. In particular, the present disclosure is directed to embodiments of a device for occluding a vascular abnormality or birth defect, such as any of a variety of atrial septal defects.

B. Background

An occluding device (or "occluder") is a medical device used to treat tissue at a target site within the human body, such as an abnormality, a vessel, an organ, an opening, a chamber, a channel, a hole, a cavity, a lumen, or the like. For example, an occluder may be used for treating atrial septal defects (ASDs). Atrial septal defects are common congenital heart defects that allow blood to flow between the left and right atria of the heart, decreasing cardiac output.

One example type of ASD is conventionally referred to as a patent foramen ovale, or PFO. In PFOs, a hole is formed, such as during fetal development, between the left and right atria. PFOs may vary in severity from generally benign to those warranting surgical intervention, such as via implantation of an occluding device, which may be implanted in the heart to repair the PFO.

In addition to PFO interventions, other percutaneous procedures are becoming more prevalent in surgical practice as well, including those for treating a variety of atrial septal defects, including as described above, but not limited to, PFOs. Conventional devices for closing ASDs include, for example, braided devices as well as many devices that include a metallic (e.g., nitinol) frame.

At least one shortcoming of such devices is that future surgical access to left and/or right atria may be limited or otherwise made more difficult by the implantation of ASD and other occluding devices. Likewise, the implantation of nitinol- and metallic-frame devices may interfere with magnetic imaging techniques (e.g., MRI), as well as pose certain allergy risks (e.g., nickel allergy). In addition, implantation of many known occluders and other ASD treatment devices may also, in at least some cases, result in erosion of and/or other disruption to the conduction system of the implanted heart.

Accordingly, it would be desirable to remove the presence of the metal frame, while maintaining the fundamental function and effectiveness of an occluder for treatment of an ASD. These and other advantages are described in additional detail herein.

SUMMARY OF THE DISCLOSURE

In one aspect, a medical device for treating an atrial septal defect (ASD) at a target site is described. The medical device includes a first occluding member, and a second occluding member disposed in opposition to the first occluding member. The medical device also includes at least one elongate shaft extending through and between the first occluding member and the second occluding member. The first occluding member is foldable to expand and contract relative to the second occluding member. The second occluding member is foldable to expand and contract relative to the first occluding member. In operation, at least one of the first occluding member and the second occluding member is configured to expand relative to the other of the first occluding member and the second occluding member to treat the ASD at the target site.

In another aspect, a delivery system for deploying a medical device to a target site is described. The delivery system includes a medical device. The medical device includes a first occluding member, and a second occluding member disposed in opposition to the first occluding member. The medical device also includes at least one elongate shaft extending through and between the first occluding member and the second occluding member. The first occluding member is foldable to expand and contract relative to the second occluding member. The second occluding member is foldable to expand and contract relative to the first occluding member. The delivery system also includes a delivery device. The delivery device includes a delivery catheter, a delivery cable within the delivery catheter and translatable with respect to the delivery catheter, and a coupling member configured to couple the medical device to the delivery cable for facilitating deployment of the medical device at the target site.

In yet another aspect, a method for treating an atrial septal defect (ASD) is described. The method includes providing medical device comprising a first occluding member, a second occluding member disposed in opposition to the first occluding member, and at least one elongate shaft extending through and between the first occluding member and the second occluding member, the first occluding member being foldable to expand and contract relative to the second occluding member, the second occluding member being foldable to expand and contract relative to the first occluding member. The method also includes advancing the medical device to the ASD using a delivery system, positioning the medical device relative to the ASD, de-coupling the medical device from the delivery system.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

Figure 1:
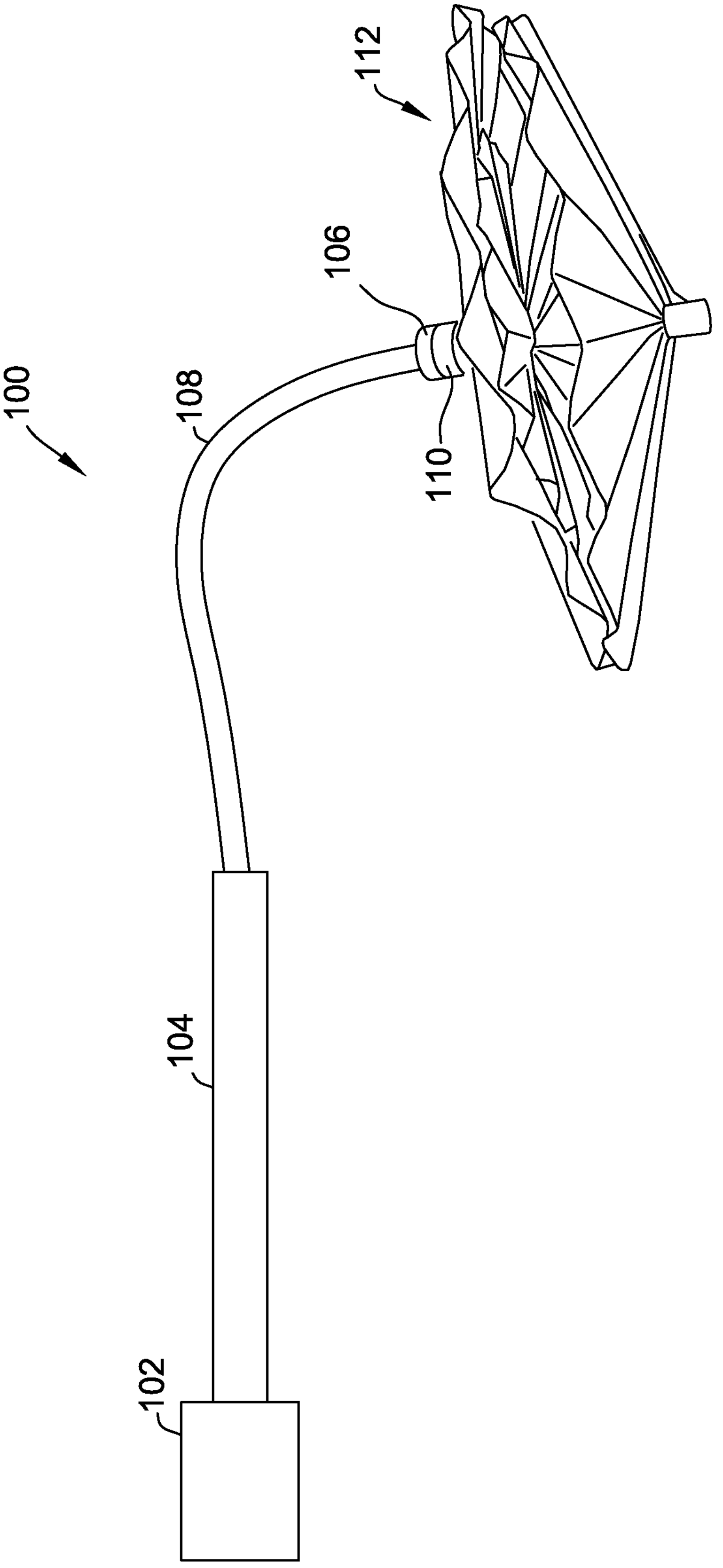
FIG. 1 is an example embodiment of a delivery system including a delivery device and a medical device in accordance with the present disclosure.

The present disclosure relates generally to medical devices that are used in the human body. Specifically, the present disclosure provides medical devices including occlusion devices having expandable and collapsible occluding members for treatment of atrial septal defects, such as patent foramen ovales (PFOs). The occlusion devices of the present disclosure may reduce the delivery profile and minimize or eliminate the amount of metallic material present in the device, compared to other known medical devices.

The disclosed embodiments may lead to more consistent and improved patient outcomes. It is contemplated, however, that the described features and methods of the present disclosure as described herein may be incorporated into any number of systems as would be appreciated by one of ordinary skill in the art based on the disclosure herein.

It is understood that the use of the term "target site" is not meant to be limiting, as the medical device may be configured to treat any target site, such as any vascular abnormality, a vessel, an organ, an opening, a chamber, a channel, a hole, a cavity, or the like, located anywhere in the body.

The term "vascular abnormality," as used herein is not meant to be limiting, as the medical device may be configured to bridge, occlude, treat, or otherwise support a variety of vascular abnormalities. For example, the vascular abnormality could be anything that affects the shape of the native lumen, such as a lesion, a vessel dissection, a PFO, any other atrial septal defect (ASD), a tumor, and the like. Embodiments of the medical device may be useful, for example, for occluding and/or treating an any such vascular abnormality.

Furthermore, the term "lumen" is also not meant to be limiting, as the vascular abnormality may reside in a variety of locations within the vasculature, such as a vessel, an artery, a vein, a passageway, an organ, an organ wall (e.g., an atrial septal wall), a cavity, or the like. For ease of explanation, the examples used herein refer to the occlusion of a patent foramen *ovale*, or PFO, as described herein.

As used herein, the term "proximal" refers to a part of the medical device or the delivery device that is closest to the operator, and the term "distal" refers to a part of the medical device or the delivery device that is farther from the operator at any given time as the medical device is being delivered through the delivery device. In addition, the terms "deployed" and "implanted" may be used interchangeably herein.

Some embodiments of the present disclosure provide an improved percutaneous catheter directed intravascular occlusion device for use in the vasculature in patients' bodies, such as blood vessels, channels, lumens, a hole through tissue, such as a hole through a portion of a heart, including a PFO, cavities, and the like. Other physiologic conditions in the body occur where it is also desirable to occlude a vessel or other passageway to prevent blood flow into or therethrough. These device embodiments may be used anywhere in the vasculature where the anatomical conditions are appropriate for the design.

As used herein, "substantially preclude or occlude flow" may be used to mean, functionally, prevention and/or reduction of blood flow for any period of time, such as during all or a portion of time that the device is implanted.

The present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout.

The medical devices of the present disclosure enable the treatment, closure, and/or sealing of an abnormality while reducing or eliminating the amount of metallic material implanted in the body, compared to known devices. Accordingly, the medical device of the present disclosure reduces or eliminates the above-described disadvantages of known medical devices while providing a sufficient treatment, closure, and/or sealing effect.

With reference to FIG. 1, a schematic diagram of a delivery system 100 is shown. Delivery system 100 includes a delivery device 102 including a catheter 104 and a coupling member 106 configured to couple a distal end of a delivery cable 108 and to a connecting member 110 of a medical device 112 for facilitating the deployment of medical device 112 at a target site. Medical device 112 is deployed to treat the target site, and, in the example embodiment, is an occlusion device ("occluder").

Figure 2:
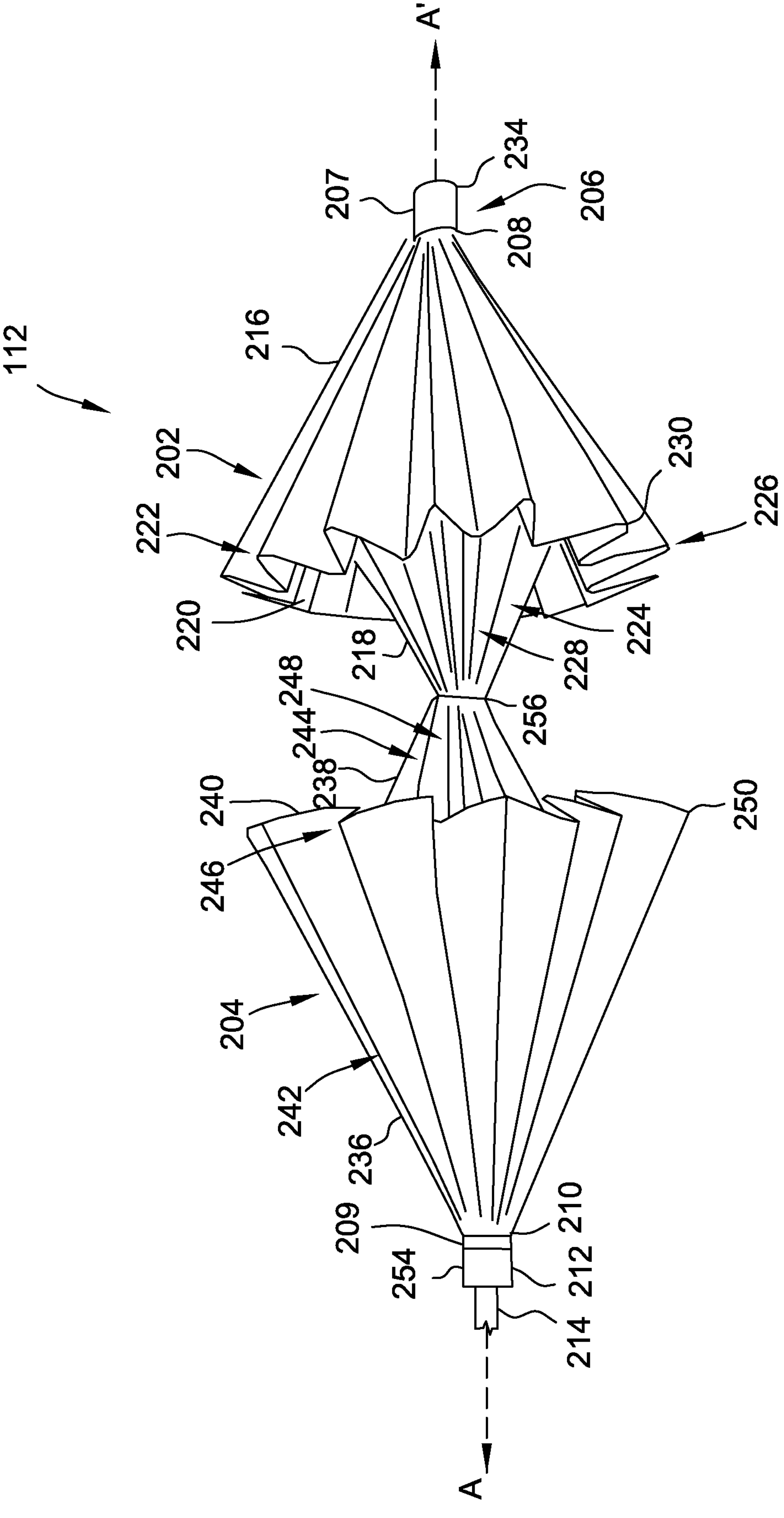
FIG. 2 illustrates a side perspective view of an example embodiment of the medical device shown in FIG. 1, in which the medical device is in a first, contracted, configuration.

FIG. 2 illustrates a side perspective view of an example embodiment of medical device 112 shown in FIG. 1, in which medical device 112 is in a first, contracted or collapsed, configuration. In the example embodiment, medical device 112 defines a centerline A-A', also referred to as a longitudinal axis of medical device 112, and includes a first occluding member 202, a second occluding member 204 disposed in substantial opposition, as shown, to first occluding member 202, and at least one elongate shaft 206 that terminates in a cap 207 at the distal end of medical device 112.

In at least some embodiments, elongate shaft 206 extends through and/or between first occluding member 202 and second occluding member 204, as shown. For example, first occluding member 202 may include a first perforation or aperture 208 oriented substantially along centerline A-A' and extending through first occluding member 202, the distal end of occluding member 202 fastened at the perforation or aperture 208 to cap 207. Likewise, second occluding member 204 may include a second perforation or aperture 210 oriented substantially along centerline A-A' and extending through second occluding member 204, the proximal end of occluding member 204 fastened at the perforation or aperture 210 to a cap 209 at the proximal end of medical device 112.

In some embodiments, cap 209 includes or functions as connecting member 110, as described further herein, by enabling connection of medical device 112 to delivery cable 108. In other embodiments, cap 207 may include or function as a connecting member 110 (e.g., for alternative delivery and deployment methods). In other embodiments, connecting member 110 (although not shown in FIG. 2) is a separate component of medical device 112 that functions substantially solely to enable delivery of medical device 112.

In the example embodiment, elongate shaft 206 is inserted through cap 209, second occluding member 204, and first occluding member 202, and coupled at its distalmost end to cap 207. Specifically, as shown, in at least the example embodiment, shaft 206 is inserted through second aperture 210 and first aperture 208, such that shaft 206 extends through and between first occluding member 202 and second occluding member 204.

Figure 7:
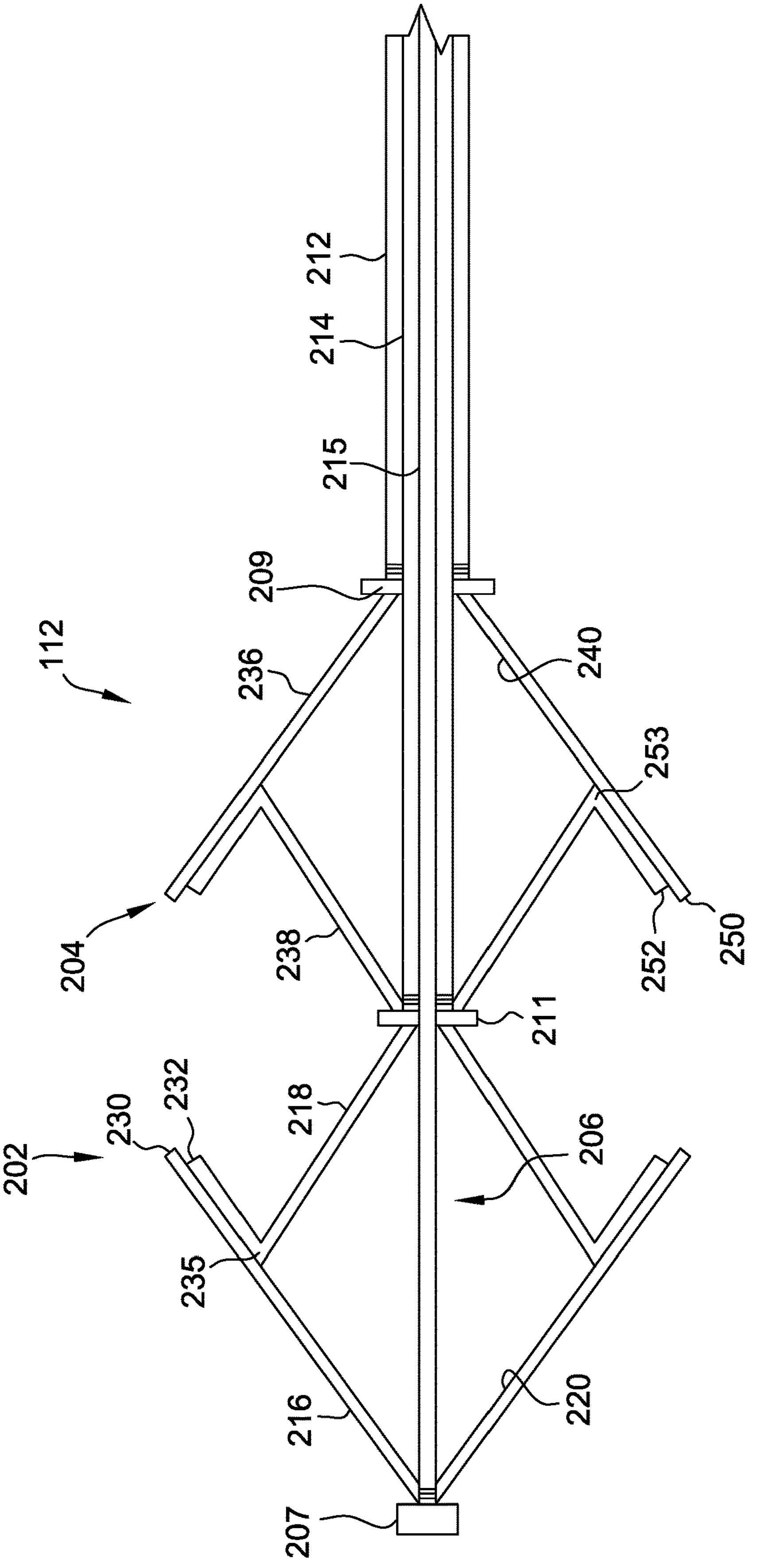
FIG. 7 depicts a cross-sectional view of an example embodiment of the medical device shown in FIGS. 1-5.

In at least some embodiments, elongate shaft 206 includes an outer shaft 212 and an inner shaft 214 disposed within outer shaft 212. For example, inner shaft 214 may be disposed radially inward of and/or coaxially with outer shaft 212, such as about centerline A-A'. In at least some embodiments, outer shaft 212 is removably coupled to cap 209—such as by a threaded connection, suture connection, or any other suitable connection—for removal of outer shaft 212 once medical device 112 has been deployed. Likewise, in at least some embodiment, inner shaft 214 is removably coupled to an intermediate cap 211 (see FIG. 7)—such as by a threaded connection, suture connection, or any other suitable connection—for removal of inner shaft 214 once medical device 112 has been deployed. In at least some embodiments, shaft 212 and/or shaft 214 are hypotubes and/or other hollow surgical grade tubes. In some embodiments, inner shaft 214 and/or outer shaft 212 may also be flexible, such as a flexible cable having a lumen therethrough. In some embodiments, as shown in FIG. 7, a third shaft 215 may also be included, such as coaxial with and positioned within or intermediate of inner shaft 214 and outer shaft 212. In at least some embodiments, third shaft 215 is removably coupled to cap 207—such as by a threaded connection, suture connection, or any other suitable connection—for removal of third shaft 215 once medical device 112 has been deployed. In some embodiments, third shaft 215 may be a hypotube or a hollow surgical grade tube (such as when positioned within inner shaft 214), or a flexible cable with a lumen therethrough (such as when positioned intermediate of inner shaft 214 and outer shaft 212). Depending on the embodiment, inner shaft 214 or third shaft 215 may be solid when serving as an innermost shaft of elongate shaft 206. For example, when serving as an innermost shaft of elongate shaft 206, inner shaft 214 or third shaft 215 may be a flexible wire (e.g., a guidewire, a pull wire, and the like).

Inner shaft 214, outer shaft 212, and/or third shaft 215 may, in at least some embodiments, also be axially translatable relative to one another. For example, third shaft 215 and/or inner shaft 214 may translate axially relative to outer shaft 212 to cause expansion and/or contraction of first occluding member 202, where for instance, at least a portion of first occluding member 202 may be coupled to inner shaft 214 and/or third shaft 215 via intermediate cap 211 and/or cap 207, respectively. Similarly, inner shaft 214 may translate axially relative to outer shaft 212 to cause expansion and/or contraction of second occluding member 204, where for example, at least a portion of second occluding member 204 may be coupled to inner shaft 214 via intermediate cap 211.

In the example embodiment, first occluding member 202 is foldable and capable of expanding and contracting relative to the second occluding member 204. Likewise, second occluding member 204 may also be foldable and capable of expanding and contracting relative to first occluding member 202. In some embodiments, first occluding member 202 and/or second occluding member 204 may not be foldable, but may nonetheless be collapsible and/or expandable, such as for example, using a flexible material. In addition, in various embodiments, the materials used for first occluding member 202 and/or second occluding member 204 may include, but are not limited to, materials such as polyurethane, polytetrafluoroethylene (PTFE), polyethylene fibers, and/or other synthetic materials and/or membranes, such as for example, membranes including fluoropolymers of tetrafluoroethylene. In some embodiments, materials may include biocompatible materials that dissolve (e.g., over a period of time, such as about one year) within the human body to facilitate healing and/or tissue growth around, within, and/or over an ASD.

Moreover, in at least some embodiments, first occluding member 202 and/or second occluding member 204 include an internal framework or scaffolding (e.g., a nitinol and/or other metallic framework). In these embodiments, the internal framework or scaffolding may further facilitate features and advantages described above when medical device 112 is implanted. In some embodiments, an internal framework, such as a nitinol framework or other supporting structure, may be included in one or both of first occluding member 202 and/or second occluding member 204. For example, in at least one embodiment, an internal framework and/or one or more support members may be included within one or both of first occluding member 202 and/or second occluding member 204, such as for example, to provide internal support, add structural stability and/or rigidity, and the like.

In the example embodiment, first occluding member 202 includes a convex portion 216 and a concave portion 218 coupled to an inner surface 220 of convex portion 216. In various embodiments, as described herein, convex portion 216 and concave portion 218 are configured to expand and contract in cooperation with one another. Convex portion 216 may also be referred to as an outer portion 216 of first occluding member 202; likewise, concave portion 218 may also be referred to as an inner portion 218 of first occluding member 202.

For example, in at least the example embodiment, outer portion 216 and inner portion 218 are foldable to facilitate expansion and contraction of first occluding member 202. More particularly, outer portion 216 and inner portion 218 each define a plurality of radially extending folds, such as a first plurality of folds 222 and a second plurality of folds 224, respectively. In the example embodiment, first plurality of folds 222 further defines a first alternating series of circumferential apices 226. Likewise, second plurality of folds 224 further defines a second alternating series of circumferential apices 228.

Figure 3:
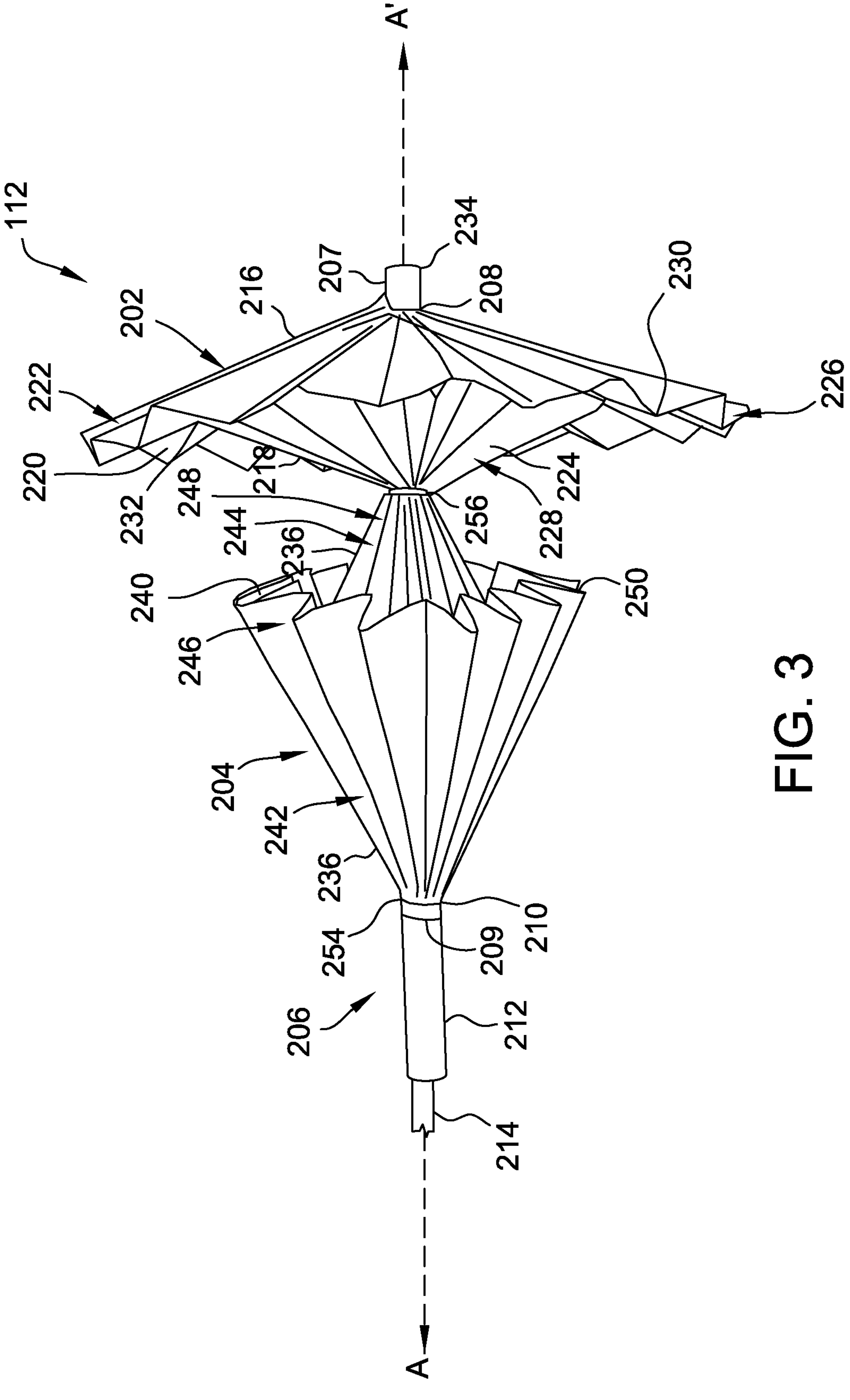
FIG. 3 illustrates a side perspective view of an example embodiment of the medical device shown in FIGS. 1 and 2, in which the medical device is in a second, partially expanded, configuration.

In addition to these features, in some embodiments, outer portion 216 defines a first radial edge 230, and inner portion 218 defines a second radial edge 232 (see FIGS. 3 and 7). As shown, first radial edge 230 is radially outward of second radial edge 232. Specifically, in at least some embodiments, first radial edge 230 is radially outward of second radial edge 232 in both an expanded as well as a contracted or collapsed configuration. As a result, it will be appreciated (e.g., as best shown with reference to FIGS. 3 and 4), that first occluding member 202 may engage with an atrial wall, during implantation and when medical device 112 is expanded or deployed, to occlude blood flow through a perforation or other ASD formed in the wall. In other embodiments, first radial edge 230 and second radial edge 232 are co-located. For example, inner portion 218 may include an intermediate fold 235 (see FIG. 7) such that inner portion 218 extends distally to intermediate fold 235 and then folds back proximally, from intermediate fold 235 to second radial edge 232.

In the example embodiment, second radial edge 232 of inner portion 218 is fastened or secured on inner surface 220 of outer portion 216, such as using an adhesive, sutures(s), and/or any other suitable fastening technique and/or materials. For example, as shown, in at least one embodiment, second radial edge 232 is fastened on inner surface 220 such that apices 226 are aligned with apices 228. However, it will be appreciated that second radial edge 232 may be secured on inner surface 220 of outer portion 216 at any location or position that best facilitates expansion and contraction of first occluding member 202 and/or during implantation, that best facilitates occlusion of an ASD.

In the example embodiment, second occluding member 204 includes a convex portion 236 and a concave portion 238 coupled to an inner surface 240 of convex portion 236. In various embodiments, as described herein, convex portion 236 and concave portion 238 are configured to expand and contract in cooperation with one another. Convex portion 236 may also be referred to as an outer portion 236 of second occluding member 204; likewise, concave portion 238 may also be referred to as an inner portion 238 of second occluding member 204.

For example, in at least the example embodiment, outer portion 236 and inner portion 238 are foldable to facilitate expansion and contraction of second occluding member 204. More particularly, outer portion 236 and inner portion 238 each define a plurality of radially extending folds, such as a first plurality of folds 242 and a second plurality of folds 244, respectively. In the example embodiment, first plurality of folds 242 further defines a first alternating series of circumferential apices 246. Likewise, second plurality of folds 244 further defines a second alternating series of circumferential apices 248.

Figure 4:
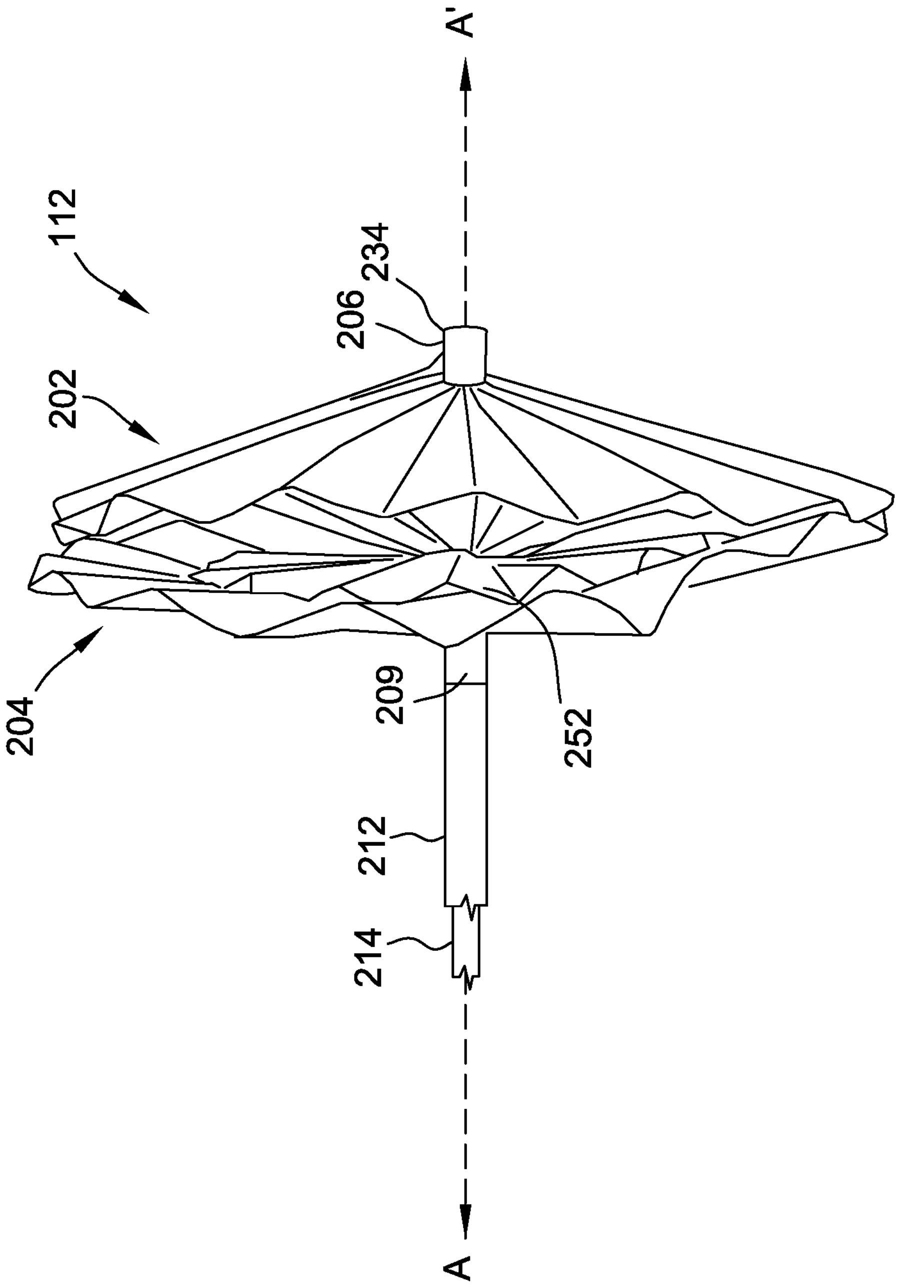
FIG. 4 illustrates a side perspective view of an example embodiment of the medical device shown in FIGS. 1-3, in which the medical device is in a third, expanded, configuration.

In addition to these features, in some embodiments, outer portion 236 defines a first radial edge 250, and inner portion 238 defines a second radial edge 252 (see FIGS. 4 and 7). As shown, first radial edge 250 is radially outward of second radial edge 252. Specifically, in at least some embodiments, first radial edge 250 is radially outward of second radial edge 252 in both an expanded as well as a contracted or collapsed configuration. As a result, it will be appreciated (e.g., as best shown with reference to FIG. 4), that second occluding member 204 may engage with an atrial wall, during implantation and when medical device 112 is expanded or deployed, to occlude blood flow through a perforation or other ASD formed in the wall. Specifically, as best shown with reference to FIG. 5, first occluding member 202 may engage a first side of an atrial wall, and second occluding member 204 may engage an opposite side of the atrial wall. In other embodiments, first radial edge 250 and second radial edge 252 are co-located. For example, inner portion 238 may include an intermediate fold 253 (see FIG. 7) such that inner portion 238 extends proximally to intermediate fold 253 and then folds back distally, from intermediate fold 253 to second radial edge 252.

In the example embodiment, second radial edge 252 of inner portion 238 is fastened or secured on inner surface 240 of outer portion 236, such as using an adhesive, stitching, and/or any other suitable fastening technique and/or materials. For example, as shown, in at least one embodiment, second radial edge 252 is fastened on inner surface 240 such that apices 246 are aligned with apices 248. However, it will be appreciated that second radial edge 252 may be secured on inner surface 240 at any location or position that best facilitates expansion and contraction of second occluding member 204 and/or during implantation, that best facilitates occlusion of an ASD.

In the example embodiment, inner portion 218 of first occluding member 202 joins inner portion 238 of second occluding member 204 at a waist 256 positioned, in at least some embodiments, substantially at a midpoint between apex 234 and apex 254. Stated another way, in at least some embodiments, waist 256 is positioned substantially at a midpoint of medical device 112. Moreover, in at least some embodiments, at least inner portion 218 and inner portion 238 are formed from a single sheet or layer of material, which may be bunched or pinched at waist 256, such as by an annular fastener, to define inner portion 218 and inner portion 238.

FIG. 3 illustrates a side perspective view of an example embodiment of medical device 112 (shown in FIGS. 1 and 2), in which medical device 112 is in a second, partially expanded, configuration. As shown, first occluding member 202 may be transitioned from a collapsed or contracted configuration, as shown in FIG. 2, to an expanded, deployed, or open configuration.

To expand first occluding member 202, in at least some embodiments, third shaft 215 may be drawn proximally while inner shaft 214 and outer shaft 212 are stabilized (e.g., by intermediate cap 211 and cap 209, respectively). More particularly, as described herein, outer portion 216 may be coupled to third shaft 215 near apex 234, via cap 207, and as third shaft 215 is drawn proximally, inner portion 218 may exert an opening force against inner surface 220 of outer portion 216 as outer portion 216 is drawn proximally with third shaft 215, which may cause both outer portion 216 and inner portion 218 to expand radially, as shown.

FIG. 4 illustrates a side perspective view of an example embodiment of medical device 112 (shown in FIGS. 1-3), in which medical device 112 is in a third, expanded, configuration. As shown, second occluding member 204 may be transitioned from a collapsed or contracted configuration, as shown in FIGS. 2 and 3, to an expanded, deployed, or open configuration.

To expand second occluding member 204, in at least some embodiments, outer shaft 212 may be advanced distally while inner shaft 214 and/or third shaft 215 are stabilized. More particularly, as described herein, outer portion 236 may be coupled to outer shaft 212 near apex 254 via cap 209, and as outer shaft 212 is advanced distally, inner portion 238 may exert an opening force against inner surface 240 of outer portion 236 as outer portion 236 is advanced distally with outer shaft 212, which may cause both outer portion 236 and inner portion 238 to expand radially, as shown. Medical device 112 may be maintained in the expanded configuration (e.g., as shown in FIG. 4, or in any intermediate configuration) based upon a friction fit between relative components (e.g., between components of shaft 206 and caps 209, 211). In other embodiments, medical device 112 includes one or more ratcheting components, snap fit components, threaded components, or components suitably configured to maintain medical device 112 in the expanded configuration upon deployment thereof.

Figure 5:
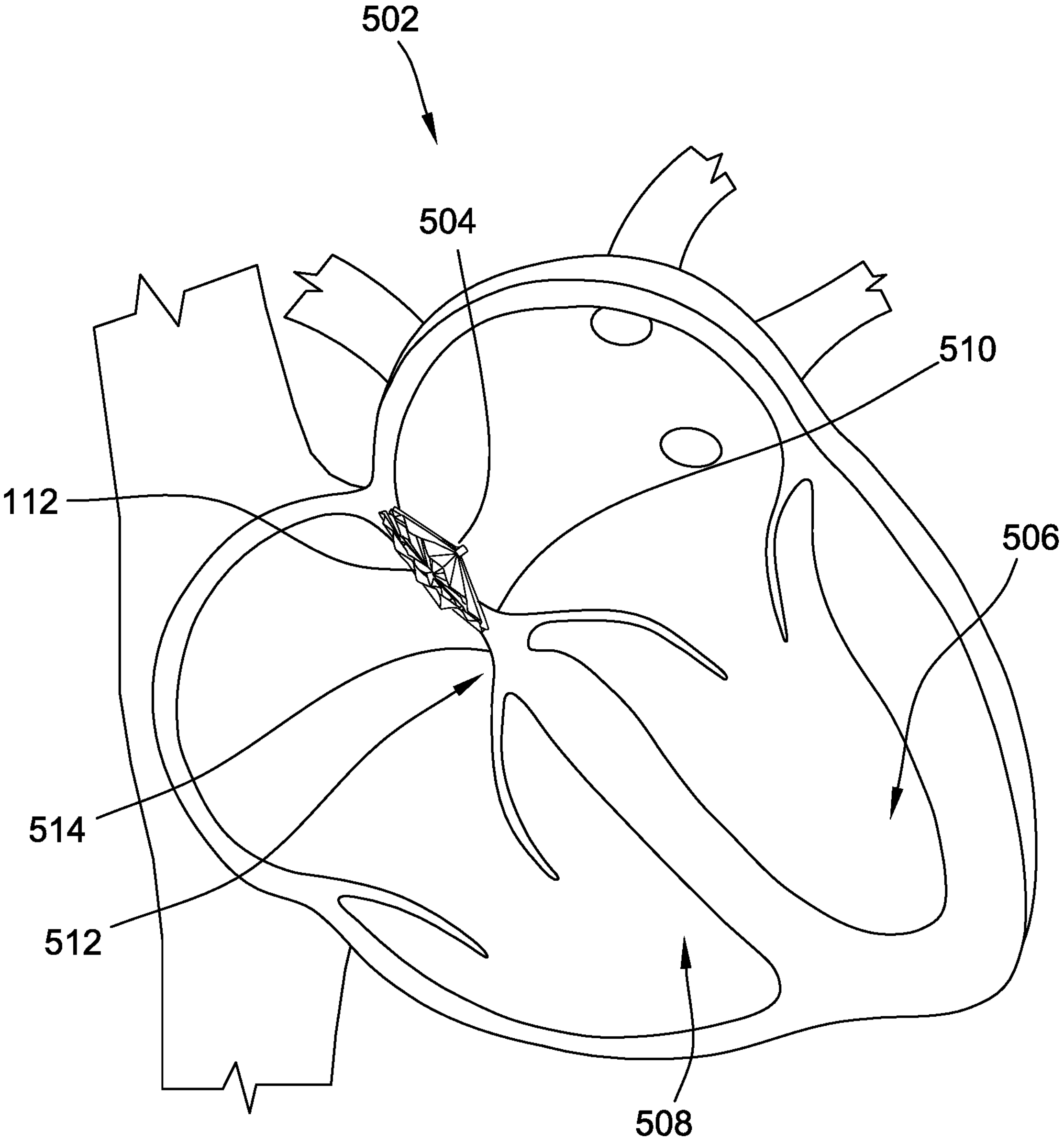
FIG. 5 illustrates a cross-sectional view of a human heart, in which an example embodiment of the medical device shown in FIGS. 1-4 is implanted in the human heart and deployed to occlude, at least partially, an atrial septal defect, such as a patent foramen *ovale*.

FIG. 5 illustrates a cross-sectional view of an example embodiment of the medical device 112 (shown in FIGS. 1-4), in which medical device 112 is implanted in a heart 502 (e.g., a human or other mammalian heart) and deployed to occlude, at least partially, an ASD 504, such as a patent foramen *ovale* (or PFO).

More particularly, to implant medical device 112, medical device 112 may be advanced, such as using delivery system 100, to ASD 504 within heart 502. Waist 256 may be positioned within ASD 504, such that first occluding member 202 is positioned in left atrium 506, and such that second occluding member 204 is positioned in right atrium 508. Alternatively, device 112 may be positioned in an opposite orientation (e.g., such that first occluding member 202 is positioned in right atrium 508 and second occluding member 204 is positioned in left atrium 506).

In addition, first occluding member 202 may be expanded, as described herein, to engage a first side 510 of an atrial wall 512 near ASD 504. Likewise, second occluding member 204 may be expanded to engage a second side 514 of atrial wall 512 near ASD 504. As a result, medical device 112 may, it will be appreciated, be positioned over and/or around ASD 504 on both sides thereof (e.g., on first side 510 and second side 514 of wall 512) to occlude, or partially occlude, blood flow through ASD 504. In some embodiments, placement of medical device 112 over ASD 504 may also facilitate tissue ingrowth and/or growth of tissue over and/or around ASD 504, such as for example, to encourage the body's natural repair and healing processes.

Figure 6:
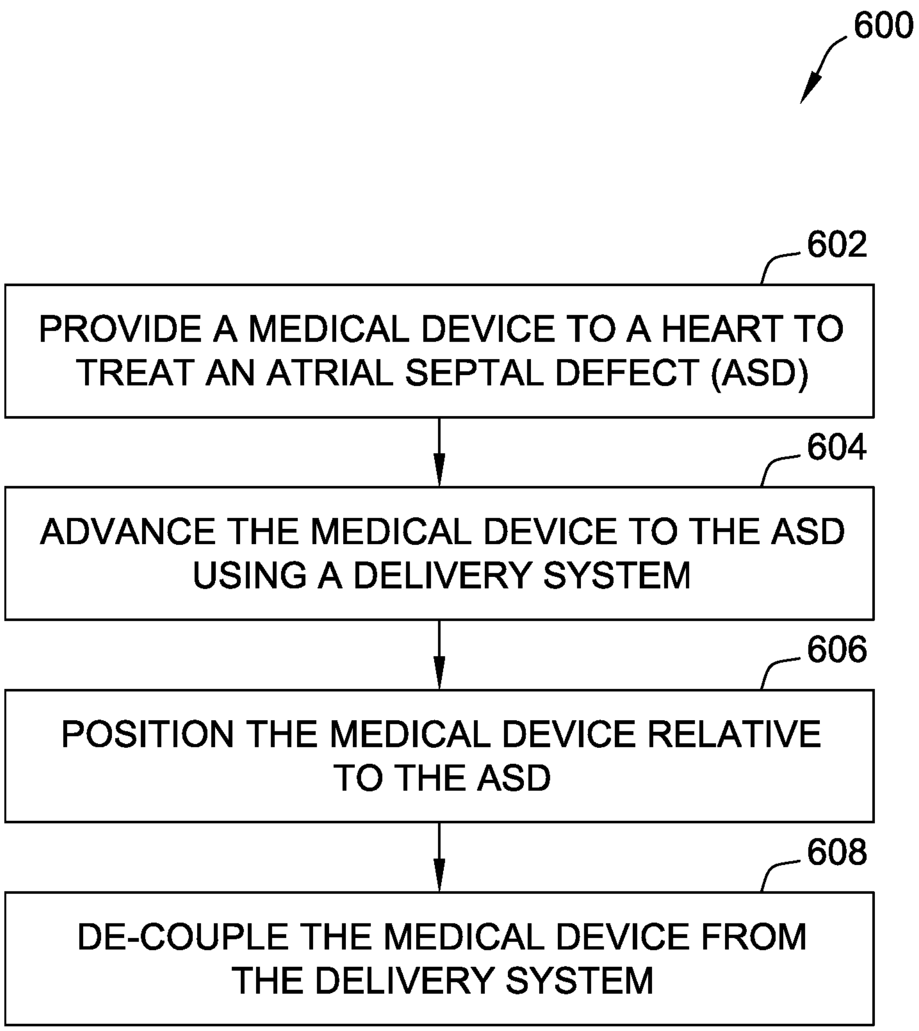
FIG. 6 is a flowchart illustrating an example embodiment of a process for delivery of the medical device shown in FIGS. 1-5 within a human body, such as within a human heart.

FIG. 6 is a flowchart illustrating an example embodiment of a process 600 for delivery of medical device (shown in FIGS. 1-5) within a human body, such as within heart 502. In the example embodiment, process 600 includes, for example, providing medical device 112, such as to heart 502 (step 602). In the example embodiment, process 600 also includes advancing medical device 112 within heart 502, such as to ASD 504 using delivery system 100 (step 604). Moreover, in at least some embodiments, process 600 includes positioning medical device 112 relative to ASD 504 (step 606). In the example embodiment, process 600 may also include de-coupling medical device 112 from delivery system 100, such as to facilitate withdrawal of delivery system 100 from heart 502, leaving medical device 112 implanted or deployed over ASD 504 to at least partially occlude blood flow therethrough (step 608).

While embodiments of the present disclosure have been described, various changes, adaptations and modifications may be made therein without departing from the spirit of the disclosure and the scope of the appended claims. Further, all directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. It is intended that all matter contained in the above description or shown in the accompanying drawings shall be interpreted as illustrative only and not limiting. Changes in detail or structure may be made without departing from the spirit of the disclosure as defined in the appended claims.

Many modifications and other embodiments of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific embodiments described and that modifications and other embodiments are intended to be included within the scope of the appended claims. Although specific terms are employed herein, they are used in a generic and descriptive sense only and not for purposes of limitation.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device for treating an atrial septal defect (ASD) at a target site, the medical device comprising:

a first occluding member including an internal framework covered by a layer of material, the first occluding member having a collapsed configuration and an expanded use configuration;

a second occluding member disposed in opposition to the first occluding member and including an internal framework covered by a layer of material, the second occluding member having a collapsed configuration and an expanded use configuration; and an elongate shaft extending through and between both the first occluding member in both the collapsed configuration and the expanded use configuration of the first occluding member and the second occluding member in both the collapsed configuration and the expanded use configuration of the second occluding member, the first occluding member being foldable to expand and collapse relative to the second occluding member, the second occluding member being foldable to expand and collapse relative to the first occluding member, wherein the elongate shaft comprises:

an outer shaft; and an inner shaft disposed within the outer shaft and extending in axial alignment with the outer shaft, wherein the inner shaft and the outer shaft are axially translatable relative to one another, wherein the first occluding member includes a first outer portion with a first end relatively close to the elongate shaft and a second end spaced away from the elongate shaft in the expanded use configuration of the first occluding member and a first inner portion with a first end relatively close to the elongate shaft and a second end spaced away from the elongate shaft in the expanded use configuration of the first occluding member, and the second end of the first inner portion is connected to the first outer portion, wherein the second end of the first outer portion defines a first radial edge, the second end of the first inner portion defines a second radial edge, and the first radial edge is radially outward of the second radial edge, wherein the second occluding member includes a second outer portion with a first end relatively close to the elongate shaft and a second end spaced away from the elongate shaft in the expanded use configuration of the second occluding member and a second inner portion with a first end relatively close to the elongate shaft and a second end spaced away from the elongate shaft in the expanded use configuration of the second occluding member, the second end of the second inner portion is connected to the second outer portion, and the layer of material at the first end of the second inner portion is directly connected to the layer of material at the first end of the first inner portion, whereby in operation, at least one of the first occluding member and the second occluding member is configured to expand relative to the other of the first occluding member and the second occluding member to treat the ASD at the target site.

2. The medical device of claim 1, wherein the first outer portion and the first inner portion are cooperatively foldable.

3. The medical device of claim 1, wherein the first radial edge is radially outward of the second radial edge both when the first occluding member is in the expanded use configuration and when the first occluding member is in the collapsed configuration.

4. The medical device of claim 1, wherein the first outer portion and the first inner portion each defines a respective plurality of radially extending folds, and each of the plurality of radially extending folds further defines an alternating series of circumferential apices.

5. The medical device of claim 1, wherein the second outer portion and the second inner portion are cooperatively foldable.

6. The medical device of claim 1, wherein the second outer portion defines a first radial edge, the second inner portion defines a second radial edge, and the first radial edge of the second outer portion is radially outward of the second radial edge of the second inner portion.

7. The medical device of claim 6, wherein the first radial edge of the second outer portion is radially outward of the second radial edge of the second inner portion both when the second occluding member is in the expanded use configuration and when the second occluding member is in the collapsed configuration.

8. The medical device of claim 1, wherein the second outer portion defines a first radial edge, the second inner portion defines a second radial edge, and the first radial edge of the second outer portion is radially co-located with the second radial edge of the second inner portion.

9. The medical device of claim 1, wherein the second outer portion and the second inner portion each defines a respective plurality of radially extending folds, and each of the plurality of radially extending folds further defines an alternating series of circumferential apices.

10. The medical device of claim 1, wherein the first occluding member is coupled to the inner shaft, and when the inner shaft is translated relative to the outer shaft, the first occluding member expands and collapses.

11. The medical device of claim 1, wherein the second occluding member is coupled to the outer shaft, and when the outer shaft is translated relative to the inner shaft, the second occluding member expands and collapses.

12. A delivery system for deploying a medical device to a target site, the delivery system comprising:

a medical device, comprising:

a first occluding member including an internal framework covered by a layer of material, the first occluding member having a collapsed configuration and an expanded use configuration;

a second occluding member disposed in opposition to the first occluding member and including an internal framework covered by a layer of material, the second occluding member having a collapsed configuration and an expanded use configuration; and an elongate shaft extending through and between both the first occluding member in both the collapsed configuration and the expanded use configuration of the first occluding member and the second occluding member in both the collapsed configuration and the expanded use configuration of the second occluding member, the first occluding member being foldable to expand and collapse relative to the second occluding member, the second occluding member being foldable to expand and collapse relative to the first occluding member, wherein the elongate shaft comprises:

an outer shaft; and an inner shaft disposed within the outer shaft and extending in axial alignment with the outer shaft, wherein the inner shaft and the outer shaft are axially translatable relative to one another;

wherein the first occluding member includes a first outer portion with a first end relatively close to the elongate shaft and a second end spaced away from the elongate shaft in the expanded use configuration of the first occluding member and a first inner portion with a first end relatively close to the elongate shaft and a second end spaced away from the elongate shaft in the expanded use configuration of the first occluding member, and the second end of the first inner portion is connected to the first outer portion, wherein the second end of the first outer portion defines a first radial edge, the second end of the first inner portion defines a second radial edge, and the first radial edge is radially outward of the second radial edge, wherein the second occluding member includes a second outer portion with a first end relatively close to the elongate shaft and a second end spaced away from the elongate shaft in the expanded use configuration of the second occluding member and a second inner portion with a first end relatively close to the elongate shaft and a second end spaced away from the elongate shaft in the expanded use configuration of the second occluding member, the second end of the second inner portion is connected to the second outer portion, and the layer of material at the first end of the second inner portion is directly connected to the layer of material at the first end of the first inner portion; and a delivery device, comprising:

a delivery catheter;

a delivery cable within the delivery catheter and translatable with respect to the delivery catheter; and a coupling member configured to couple the medical device to the delivery cable for facilitating deployment of the medical device at the target site.

13. The delivery system of claim 12, wherein the first outer portion and the first inner portion each defines a respective plurality of radially extending folds, and each of the plurality of radially extending folds further defines an alternating series of circumferential apices.

* * * * *